US005834593A

United States Patent [19]
Prusiner et al.

[11] Patent Number: 5,834,593
[45] Date of Patent: Nov. 10, 1998

[54] SOLUBLE FORM OF PRP$^{SC}$ WHICH IS INSOLUBLE IN NATIVE FORM

[75] Inventors: Stanley B. Prusiner; Fred E. Cohen; Tamaki Muramoto, all of San Francisco, Calif.

[73] Assignee: The Regents of the University of California, Oakland, Calif.

[21] Appl. No.: 740,947

[22] Filed: Nov. 5, 1996

[51] Int. Cl.$^6$ ............................. C07K 1/00; C07K 14/00; C07K 16/00; C07K 17/00
[52] U.S. Cl. ........................... 530/350; 530/356; 435/6; 435/7.1; 435/2.3; 435/72.3; 435/236
[58] Field of Search .................................. 530/350, 356; 435/236, 23, 6, 7.1, 172.3

[56] References Cited

U.S. PATENT DOCUMENTS

| | | |
|---|---|---|
| 5,182,366 | 1/1993 | Huebner et al. . |
| 5,387,746 | 2/1995 | Whitsett . |
| 5,420,246 | 5/1995 | Rutter et al. . |
| 5,552,381 | 2/1994 | Atkinson ................................. 514/8 |
| 5,565,186 | 10/1996 | Prusiner et al. . |
| 5,605,691 | 9/1993 | Carroll .............................. 424/184.1 |

FOREIGN PATENT DOCUMENTS

WO 93/10227  5/1993  WIPO .

OTHER PUBLICATIONS

Shigematsu et al. J. Biol. Chem. 267(30):21329–37, Oct. 25, 1992.
Strandberg et al. Appl. Environ. Microbiol. 57(6):1669–74, Jun. 1991.
Tabliavini et al. Biochem. Biophys. Res. Comm. 184(3):1398–1404, May 15, 1992.
Zhang et al. J. Biol. Chem. 269(45):27799–27802 Nov. 11, 1994.
H. Büeler et al "Normal development of mice lacking the neuronal cell–surface PrP protein" *Nature* 356, 577–582 (1992).
K. R. Thomas et al. "Site directed mutagenesis by gene targeting in mouse embryo–derived stem cells,"*Cell* 51:503–512 (1987).
B.W. Caughey, et al., "Secondary structure analysis of the scrapie–associated protein PrP 27–30 in water by infrared spectroscopy,"*Biochemistry 30*, 7672–7680 (1991).
B. Caughey, et al., "Aggregates of scrapie–associated prion protein induce the cell–free conversion of protease–sensitive prion protein to the protease–resistant state,"*J. Chem. Biol. 2*, 807–817 (1995).
G. Chazot, et al., "New variant of Creutzfeldt–Jakob disease in a 26–year old French man,"*Lancet 347*:1181 (1996).
F.E. Cohen, et al., "Structural clues to prion replication, "*Science 264*:530–531 (1994).
M. Fischer, et al., "Prion protein (PrP) with amino–proximal deletions restoring susceptibility of PrP knockout mice to scrapie,"*EMBO J. 15*(6):1255–64 (1996).
R. Gabizon, et al., "Properties of scrapie prion protein Liposomes,"*J. Biol. Chem. 263*:4950–4955 (1988).

J. Gabriel et al., "Molecular cloning of a candidate chicken prion protein," *Proc. Natl. Acad. Sci. USA 89*:9097–9101 (1992).
M. Gasset, et al., "Predicted α–helical regions of the prion protein when synthesized as peptides form amyloid," *Proc. Natl. Acad. Sci. USA 89*:10940–10944 (1992).
M. Gasset, et al., "Perturbation of the secondary structure of the scrapie prion protein under conditions that alter infectivity," *Proc. Natl. Acad. Sci. USA 90*:1–5 (1993).
D.A. Kocisko, et al., "Cell–free formation of protease–resistant prion protein," *Nature 370*, 471–474 (1994).
Z. Huang, et al., "Proposed three–dimensional structure for the cellular prion protein," *Proc. Natl. Acad. Sci. USA 91*:7139–7143 (1994).
Z. Huang, et al., "Scrapie prions: a three–dimensional model of an infectious fragment," *Folding & Design 1*:13–19 (1995).
C. Locht, et al., "Molecular cloning and complete sequence of prion protein cDNA from mouse brain infected with the scrapie agent," *Proc. Natl. Acad. Sci. USA 83*: 6372–6276 (1986).
I. Mehlhorn, et al., "High–level expression and characterization of a purified 152–residue polypeptide of the prion protein," *Biochemistry 35*:5528–5537 (1996).
R.K. Meyer, et al., "Separation and properties of cellular and scrapie prion proteins," *Proc. Natl. Acad. Sci. USA 83*:2310–2314 (1986).
J. Nguyen, et al., "Prion protein peptides induce α–helix to β–sheet conformational transitions," *Biochemistry 34*:4186–4192 (1995).
K.M. Pan, et al., "Conversion of α–helices into β–sheets features in the formation of the scrapie prion proteins," *Proc. Natl. Acad. Sci. USA 90*:10962–10966 (1993).

(List continued on next page.)

*Primary Examiner*—Lila Feisee
*Assistant Examiner*—Lin Sun-Hoffman
*Attorney, Agent, or Firm*—Bozicevic & Reed LLP; Karl Bozicevic

[57] ABSTRACT

The invention includes deleting codon segments from DNA expressing a native protein (e.g., PrP$^{Sc}$) in order to obtain a shorter, soluble protein which mimics characteristics of an insoluble native (e.g., PrP$^{Sc}$) protein. Soluble proteins of the invention are characterized by: (1) having less amino acids than the full length native protein; (2) having a higher degree of solubility than the native protein; (3) retaining the basic biological characteristics of the native protein such as (a) not being subject to enzymatic digestion and (b) causing disease. Soluble proteins of the invention are obtained by providing a DNA sequence which encodes a native protein and systematically removing codons, making copies of the shortened versions of DNA which are then expressed to provide the shortened proteins. The shortened proteins are then tested for solubility. Soluble proteins are then further tested to confirm that they retain the biological characteristics of the native protein. The soluble form can also be created by adding amino acids, binding a hydrophilic moiety to the native protein or combinations of deleting, adding, and binding hydrophilic moieties to the protein.

4 Claims, 1 Drawing Sheet

OTHER PUBLICATIONS

S.B. Prusiner, et al., "Further purification and characterization of scrapie prions," *Biochemistry 21*:6942–6950 (1982).

S.B. Prusiner, et al., "Scrapie prions aggregate to form amyloid–like birefringent rods," *Cell 35 (2)*:349–358 (1983).

S.B. Prusiner, et al., "Purification and structural studies of a major scrapie prion protein," *Cell 38*:127–134 (1984).

R. Riek, et al., "NMR structure of the mouse prion protein domain PrP(121–231)," *Nature 382*:180–182 (1996).

M. Rogers, et al., "Epitope mapping of the syrian hamster prion protein utilizing chimeric and mutant genes in a vaccinia virus expression system," *J. Immunol.* 147:3568–3574 (1991).

M. Rogers, et al., "Conversion of truncated and elongated prion proteins into the scrapie isoform in cultured cells," *Proc. Natl. Acad. Sci. USA 90*:3182–3186 (1993).

J. Safar, et al., "Conformational transitions, dissociation, and unfolding of scrapie amyloid (prion) protein," *J. Biol. Chem. 268*:20276–20284 (1993).

M. Scott, et al., "Prion protein gene expression in cultured cells," *Protein Engineering 2*:69–76 (1988).

M.R. Scott, et al., "Chimeric prion protein expression in cultured cells and transgenic mice," *Protein Sci.* 1:986–997 (1992).

N. Stahl, et al., "Scrapie prion protein contains a phosphatidylinositol glycolipid," *Cell 51*:229–240 (1987).

A. Taraboulos, et al., "Acquisition of protease resistance by prion proteins in scrapie–infected cells does not require asparagine–linked glycosylation," *Proc. Natl. Acad. Sci. USA 87*:8262–6.

A. Taraboulos, et al., "Cholesterol depletion and modification of COOH–terminal targeting sequence of the prion protein inhibit formation of the scrapie isoform," *J. Cell Biol.* 129:121–132 (1995).

E. Turk, et al., "Purification and properties of the cellular and scrapie hamster prion proteins," *Eur. J. Biochem.* 176:21–30 (1988).

R.G. Will, et al., "New variant of Creuzfeldt–Jacob disease in the UK," *Lancet 347*, 921–925 (1996).

R. A. Williamson, et al., "Circumventing tolerance to generate autologous monoclonal antibodies to the prion protein," *Proc. Natl. Acad. Sci. USA 93*:7279–7282 (1996).

C.S. Yost, et al., "Non–hydrophobic extracytoplasmic determinant of stop transfer in the prion protein," *Nature 343*:669–672 (1990).

H, Zhang, et al., "Conformational transitions in peptides containing two putative α–helices of the prion protein," *J. Mol. Biol.* 250:514–526 (1995).

FIG. 1

SOLUBLE FORM OF PRP$^{Sc}$ WHICH IS INSOLUBLE IN NATIVE FORM

STATEMENT AS TO FEDERALLY SPONSORED RESEARCH

Material disclosed in this application was developed, in part, with grants from the National Institute of Health via Grants NS14069, AG08967, AG02132, NS22786 and AG10770 and the American Health Assistance Foundation. The government may have certain rights in this material.

FIELD OF THE INVENTION

This invention relates generally to the field of molecular genetics and more particularly to methods of making insoluble proteins soluble and to the soluble proteins and derivative thereof.

BACKGROUND OF THE INVENTION

A number of naturally occurring proteins are known to be insoluble and to be related to a particular disease state. Examples include β amyloid protein plaques associated with Alzheimer's disease, Lewy bodies or Pick bodies associated with Parkinson's and Pick's diseases and prion proteins (i.e., PrP$^{Sc}$) associated with Creutzfeldt-Jakob disease (CJD) and other neurological disorders. The PrP gene of mammals expresses a protein which can be the soluble, non-disease form PrP$^C$ or be converted to the insoluble, disease form or PrP$^{Sc}$. There are also a number of systemic diseases which are associated with protein aggregation including multiple myeloma, carcinomas of the thyroid and Congophilic angiopathies.

The importance of understanding the conversion of PrP$^C$ into PrP$^{Sc}$ has been heightened by the possibility that bovine prions have been transmitted to humans who developed variant Creutzfeldt-Jakob disease (vCJD), G. Chazot, et al., Lancet 347, 1181 (1996); R. G. Will, et al., Lancet 347, 921–925 (1996). Earlier studies had shown that the N-terminus of PrP$^{Sc}$ could be truncated without loss of scrapie infectivity, S. B. Prusiner, et al., Biochemistry 21, 6942–6950 (1982); S. B. Prusiner, et al., Cell 38, 127–134 (1984) and correspondingly, the truncation of the N-terminus of PrP$^{Sc}$ still allowed its conversion into PrP$^{Sc}$ M. Rogers, et al., Proc. Natl. Acad. Sci. USA 90, 3182–3186 (1993). However, any form of PrP$^{Sc}$ (i.e., the protein form which causes disease) is also insoluble. The insolubility of the protein makes it difficult to analyze and greatly hinders efforts of generating an antibody which binds to the protein. Further, the soluble form of the protein (i.e., PrP$^C$) is known to (1) be digestible with enzymes that do not digest PrP$^{Sc}$ and (2) not cause disease.

SUMMARY OF THE INVENTION

The insolubility of certain proteins associated with diseases has made it difficult to carry out structural analysis of such proteins or to generate antibodies specific for these proteins. The present invention provides soluble forms of such proteins. This can be obtained in different ways such as by (1) systematically removing segments of DNA encoding the native protein or (2) adding DNA and then expressing the modified protein or (3) chemically modifying the insoluble protein such as by adding amino acids with hydrophilic side chains or other hydrophilic groups. The resulting protein (1) is soluble, (2) cannot be digested by enzymes which digest the native soluble form and (3) retains its biological function (e.g. maintains abnormal properties associated with disease).

The synthetic soluble forms of these proteins are useful in generating antibodies which selectively bind the modified soluble proteins as well as the insoluble native proteins. The soluble proteins can also be used to screen drugs with respect to their effect on the protein in terms of the drugs ability to eliminate the proteins abnormal properties associated with disease.

A soluble form of a naturally occurring insoluble protein, such as a soluble form of native PrP$^{Sc}$ is produced by the process described herein. Although other processes might be used to obtain a soluble form of proteins which are insoluble in their native form, this invention encompasses soluble proteins of the type described herein produced by other methods. The general method involves first determining the DNA sequence which encodes a protein which is either expressed in an insoluble form or later converted to an insoluble protein, which insoluble protein is associated with a disease of the nervous system. Copies of the DNA sequence are then made. Using the individual copies or groups of copies, a portion or portions of the DNA are removed. The removal is, of course, made in codon segments, thereby providing a plurality of different DNA sequences which are different from each other in view of the different codon sequences removed. These different shortened sequences are then expressed and a plurality of different proteins obtained. The different proteins obtained are tested for solubility. Proteins which are soluble are then tested with respect to other activity such as whether the protein can be digested by enzymes which normally do not digest the insoluble protein. If the protein is both soluble and resistant to digestion, it can be further tested for biological activity. For example, the protein can be used to inoculate an animal which would normally develop disease when inoculated with the insoluble native form of the protein. If the inoculated animal develops disease, then the protein is part of the present invention and characterized as (1) soluble; (2) not subject to enzymatic digestion; (3) biologically active, e.g., with respect to its ability to cause disease and/or generate antibodies which bind the insoluble native protein.

An object of the invention is to provide soluble forms of proteins which are insoluble in nature which soluble forms maintain biological characteristics of the insoluble native form.

A more specific object is to provide a soluble form of PrP$^{Sc}$ (i.e., a soluble prion) which maintains the biological disease causing characteristics of insoluble, native PrP$^{Sc}$ and which generate antibodies which bind PrP$^{Sc}$.

Another object of the invention is to provide a method for systematically removing or adding segments of DNA to obtain shorter or longer sequences which express a soluble form of a disease causing protein which is insoluble in native form.

Another object is to provide proteins which converts insoluble native proteins to a soluble form which is then degraded thereby providing proteins useful in the treatment of diseases associated with the insoluble proteins.

Another object of the invention is to provide antibodies and methods of producing such antibodies using the soluble proteins of the invention, wherein the antibodies bind to the native insoluble form of the protein.

Another object of the invention is to provide a method for producing a soluble form of a protein that is capable, in vivo, of binding to an aggregation prone form of the protein resulting in a complex which retards, reverses or completely stops protein aggregation associated with a disease.

Another object is to provide assay devices which are comprised of supports having antibodies bound to their surface wherein the antibodies are generated using the soluble proteins of the invention.

An advantage of the invention is that soluble proteins are more easily subjected to structural analysis and facilitate the ability to generate antibodies as compared to insoluble proteins.

A feature of the invention is that the soluble proteins of the invention maintain important biological functions of native insoluble proteins.

Another feature is that the soluble protein having abnormal properties associated with disease can be used to screen for drugs which convert the protein to its non-disease conformation.

These and other objects, advantages and features of the invention will become apparent to those skilled in the art upon reading this disclosure.

DETAILED DESCRIPTION OF PREFERRED EMBODIMENTS

Before the present soluble proteins and methods of making such are described, it is to be understood that this invention is not limited to the particular proteins, methods, antibodies or processes described as such may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "and," and "the" include plural referents unless the contexts clearly dictates otherwise. Thus, for example, reference to "a protein" includes mixtures and large numbers of proteins, reference to "an antibody" includes large numbers of antibodies and mixtures thereof, and reference to "the method" includes one or more methods or steps of the type described herein.

The publications discussed herein are provided solely for their disclosure prior to the filing date of the present application. Nothing herein is to be construed as an admission that the present invention is not entitled to antedate such publication by virtue of prior invention.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications cited herein are incorporated herein by reference for the purpose of disclosing and describing specific aspects of the invention for which the publication is cited with connection with.

DEFINITIONS

The term "soluble" shall mean a property of a compound with respect to its ability to mix within a liquid and specifically shall mean its ability to dissolve in a liquid such as water, an aqueous salt, a mixed solvent or detergent solution to form a homogenous mixture, i.e., a solution and not merely a suspension. The solubility of a protein per the present invention can be defined using a variety of different parameters and those parameters can change depending on the particular protein whose solubility is being measured. In general, insoluble native proteins which are associated with disease states are insoluble in water, salt solutions and mild detergents (i.e., detergents which do not denature the protein) whereas soluble proteins of the invention are soluble in one or all of these. Further, soluble proteins of the invention can be placed in solution and subjected to 100,000 g for one hour and will remain in the supernatant. The protein $PrP^{Sc}$ 106 of the present invention is soluble in an aqueous solution of a mild detergent which does not denature the protein or the native $PrP^{Sc}$. When $PrP^{Sc}$ 106 is placed in aqueous solution of a mild detergent and subjected to 100,000 g in a centrifuge for one hour the protein $PrP^{Sc}$ 106 remains in the supernatant. A variety of different detergents can be used when checking the solubility of the modified protein. One suitable example of detergent compositions includes a combination of 0.5% sodium deoxycholate; 0.5% Triton X-100 and Sarkosyl in an amount of 0.5%; 1.0% or 2.0% as needed. The protein $PrP^{Sc}$ 106 is soluble in any of the three concentrations of Sarkosyl. In addition to including a detergent within the solvent it is preferable to include a salt and to maintain the pH in the range of 5 to 9, more preferably 6 to 8 and still more preferably about 7.5. Examples of salts which can be used include 10 mM of Tris-HCl at a pH of 7.5; 100 mM NaCl (sodium chloride); or 1 mM EDTA. Other salts within concentrations within the range of 1 mM to 100 mM can also be used. For example a soluble $PrP^{Sc}$ protein has twice the solubility or more as native $PrP^{Sc}$ protein and preferably five times the solubility of native $PrP^{Sc}$ protein while maintaining its ability to cause disease in a mammal.

The term "insoluble" shall be used herein to described a characteristic of a compound, and specifically a characteristic of a protein with respect to its ability to not mix with a liquid and not dissolve within a liquid in order to form a homogenous mixture and specifically not to dissolve in water or an aqueous salt or detergent solution. Insoluble native proteins of the type described herein shall be designated insoluble when the protein is not in the supernatant after subjecting the protein to 100,000 g for one hour when the protein is in water, water and a salt, water and a detergent which does not denature the protein or water, salt and a detergent which does not denature the protein.

The terms "digestible" and "subject to enzymatic digestion" and the like are used interchangeably herein and shall mean that a protein is cleaved by an enzyme into two or more pieces and preferably cleaved into a plurality (i.e., three or more pieces) when brought into contact with the enzyme under conditions at which the enzyme would normally be expected to cleave a protein.

The particular enzyme or enzymes used, the length of time the enzyme is brought into contact with the protein and other conditions such as temperature and pressure will vary depending on the particular modified protein being tested. When carrying out digestion tests on proteins expressed by modifying the PrP gene it is preferable to use protease K and to bring protease K into contact with the protein for a period of time in the range of about 10 minutes to 2 hours more preferably 20 minutes to 1 hour and still more preferably about 30 minutes at a temperature in the range of above 0° C. and less than 100° C. more preferably 15° to 45° C. and still more preferably about 37° C. at atmospheric pressure. If the protein is denatured when exposed to protease K for about 30 minutes at about 37° C. then the protein does not possess the biological characteristics of the native $PrP^{Sc}$ protein which causes disease. If the protein is not digested then the protein can be further tested for its ability to cause disease and be classified as a protein of the present invention.

The terms "not digestible" and "not subject to enzymatic digestion" are used interchangeably herein and shall mean that when a protein is brought into contact with an enzyme the protein is not cleaved. Specifically, the term shall mean that the protein remains in one piece and is not divided when the enzyme is brought into contact with the protein under conditions which would normally result in cleavage of the protein.

The terms "PrP protein", "PrP" and the like are used interchangeably herein and shall mean both the infectious particle form $PrP^{Sc}$ known to cause diseases (spongiform encephalopathies) in humans and animals and the non-infectious form $prP^C$ which, under appropriate conditions is converted to the infectious $PrP^{Sc}$ form.

The terms "prion", "prion protein" and "$PrP^{Sc}$ protein" and the like used interchangeably herein to refer to the infectious $PrP^{Sc}$ form of a PrP protein and is a contraction of the words "protein" and "infection" and the particles are comprised largely if not exclusively of $PrP^{Sc}$ molecules encoded by a PrP gene. Prions are distinct from bacteria, viruses and viroids. Known prions include those which infect animals to cause scrapie, a transmissible, degenerative disease of the nervous system of sheep and goats as well as bovine spongiform encephalopathies (BSE) or mad cow disease and feline spongiform encephalopathies of cats. Four prion diseases known to affect humans are (1) kuru, (2) Creutzfeldt-Jakob Disease (CJD), (3) Gerstmann-Strassler-Scheinker Disease (GSS), and (4) fatal familial insomnia (FFI). As used herein prion includes all forms of prions causing all or any of these diseases or others in any animals used—and in particular in humans and in domesticated farm animals.

The term "PrP gene" is used herein to describe genetic material which expresses proteins as shown in FIGS. 2–4 of U.S. Pat. No. 5,565,186 issued Oct. 15, 1996, and polymorphisms and mutations such as those listed herein under the subheading "Pathogenic Mutations and Polymorphisms" of U.S. Pat. No. 5,565,186. The term "PrP gene" refers generally to any gene of any species which encodes any form of a prion protein. Some commonly known PrP sequences are described in Gabriel et al., *Proc. Natl. Acad. Sci. USA* 89:9097–9101 (1992) which is incorporated herein by reference to disclose and describe such sequences. The PrP gene can be from any animal including the "host" and "test" animals described herein and any and all polymorphisms and mutations thereof, it being recognized that the terms include other such PrP genes that are yet to be discovered. The protein expressed by such a gene can assume either a $PrP^C$ (non-disease) of $PrP^{Sc}$ (disease) form.

The terms "standardized prion preparation", "prion preparation", "preparation" and the like are used interchangeably herein to describe a composition containing prions ($PrP^{Sc}$) which composition is obtained from brain tissue of mammals which contain substantially the same genetic material as relates to prions, e.g., brain tissue from a set of mammals which exhibit signs of prion disease which mammals (1) include a transgene as described herein; (2) have an ablated endogenous prion protein gene; (3) have a high copy number of prion protein gene from a genetically diverse species; or (4) are hybrids with an ablated endogenous prion protein gene and a prion protein gene from a genetically diverse species. The mammals from which standardized prion preparations are obtained exhibit clinical signs of CNS dysfunction as a result of inoculation with prions and/or due to developing the disease due to their genetically modified make up, e.g., high copy number of prion protein genes.

The term "artificial PrP gene" is used herein to encompass the term "chimeric PrP gene" as well as other recombinantly constructed genes which when included in the genome of a host animal (e.g., a mouse) will render the mammal susceptible to infection from prions which naturally only infect a genetically diverse test mammal, e.g., human, bovine or ovine. In general, an artificial gene will include the codon sequence of the PrP gene of the mammal being genetically altered with one or more (but not all, and generally less than 40) codons of the natural sequence being replaced with a different codon—preferably a corresponding codon of a genetically diverse mammal (such as a human). The genetically altered mammal being used to assay samples for prions which only infect the genetically diverse mammal. Examples of artificial genes are mouse PrP genes encoding the sequence as shown in FIGS. 2, 3 and 4 of U.S. Pat. No. 5,565,186 with one or more different replacement codons selected from the codons shown in these Figures for humans, cows and sheep replacing mouse codons at the same relative position, with the proviso that not all the mouse codons are replaced with differing human, cow or sheep codons. Artificial PrP genes can include not only codons of genetically diverse animals but may include codons and codon sequences not associated with any native PrP gene but which, when inserted into an animal render the animal susceptible to infection with prions which would normally only infect a genetically diverse animal.

The terms "chimeric gene," "chimeric PrP gene", "chimeric prion protein gene" and the like are used interchangeably herein to mean an artificially constructed gene containing the codons of a host animal such as a mouse with one or more of the codons being replaced with corresponding codons from a genetically diverse test animal such as a human, cow or sheep. In one specific example the chimeric gene is comprised of the starting and terminating sequence (i.e., N- and C-terminal codons) of a PrP gene of a mammal of a host species (e.g. a mouse) and also containing a nucleotide sequence of a corresponding portion of a PrP gene of a test mammal of a second species (e.g. a human). A chimeric gene will, when inserted into the genome of a mammal of the host species, render the mammal susceptible to infection with prions which normally infect only mammals of the second species. The chimeric gene MHu2M contains the starting and terminating sequence of a mouse PrP gene and a non-terminal sequence region which is replaced with a corresponding human sequence which differs from a mouse PrP gene in a manner such that the protein expressed thereby differs at nine residues.

The term "genetic material related to prions" is intended to cover any genetic material which effects the ability of an animal to become infected with prions. Thus, the term encompasses any "PrP gene", "artificial PrP gene", "chimeric PrP gene" or "ablated PrP gene" which terms are defined herein as well as modification of such which effect the ability of an animal to become infected with prions. Standardized prion preparations are produced using animals which all have substantially the same genetic material related to prions so that all of the animals will become infected with the same type of prions and will exhibit signs of infection at about the same time.

The terms "host animal" and "host mammal" are used to describe animals which will have their genome genetically and artificially manipulated so as to include genetic material which is not naturally present within the animal. For example, host animals include mice, hamsters and rats which have their PrP gene ablated i.e., rendered inoperative. The host is inoculated with prion proteins to generate antibodies. The cells producing the antibodies are a source of genetic material for making a phage library. Other host animals may have a natural (PrP) gene or one which is altered by the insertion of an artificial gene or by the insertion of a native PrP gene of a genetically diverse test animal.

The terms "test animal" and "test mammal" are used to describe the animal which is genetically diverse from the host animal in terms of differences between the PrP gene of the host animal and the PrP gene of the test animal. The test animal may be any animal for which one wishes to run an assay test to determine whether a given sample contains prions with which the test animal would generally be susceptible to infection. For example, the test animal may be a human, cow, sheep, pig, horse, cat, dog or chicken, and one may wish to determine whether a particular sample includes prions which would normally only infect the test animal.

The terms "genetically diverse animal" and "genetically diverse mammal" are used to describe an animal which includes a native PrP codon sequence of the host animal which differs from the genetically diverse test animal by 17 or more codons, preferably 20 or more codons, and most preferably 28–40 codons. Thus, a mouse PrP gene is genetically diverse with respect to the PrP gene of a human, cow or sheep, but is not genetically diverse with respect to the PrP gene of a hamster.

The terms "ablated PrP protein gene", "disrupted PrP gene", and the like are used interchangeably herein to mean an endogenous PrP gene which has been altered (e.g., add and/or remove nucleotides) in a manner so as to render the gene inoperative. Examples of nonfunctional PrP genes and methods of making such are disclosed in Büeler, H., et al "Normal development of mice lacking the neuronal cell-surface PrP protein" Nature 356, 577–582 (1992) and Weisman (WO 93/10227). The methodology for ablating a gene is taught in Capecchi, Cell 51:503–512 (1987) all of which are incorporated herein by reference. Preferably both alleles of the genes are disrupted.

The terms "hybrid animal", "transgenic hybrid animal" and the like are used interchangeably herein to mean an animal obtained from the cross-breeding of a first animal having an ablated endogenous prion protein gene with a second animal which includes either (1) a chimeric gene or artificial PrP gene or (2) a PrP gene from a genetically diverse animal. For example a hybrid mouse is obtained by cross-breeding a mouse with an ablated mouse gene with a mouse containing (1) human PrP genes (which may be present in high copy numbers) or (2) chimeric genes. The term hybrid includes any offspring of a hybrid including inbred offspring of two hybrids provided the resulting offspring is susceptible to infection with prions with normal infect only a genetically diverse species. A hybrid animal can be inoculated with prions and serve as a source of cells for the creation of hybridomas to make monoclonal antibodies of the invention.

The terms "susceptible to infection" and "susceptible to infection by prions" and the like are used interchangeably herein to describe a transgenic or hybrid test animal which develops a disease if inoculated with prions which would normally only infect a genetically diverse test animal. The terms are used to describe a transgenic or hybrid animal such as a transgenic mouse Tg(MHu2M) which, without the chimeric PrP gene, would not become infected with a human prion but with the chimeric gene is susceptible to infection with human prions.

By "antibody" is meant an immunoglobulin protein which is capable of binding an antigen. Antibody as used herein is meant to include the entire antibody as well as any antibody fragments (e.g. $F(ab')_2$, Fab', Fab, Fv) capable of binding the epitope, antigen or antigenic fragment of interest.

Antibodies of the invention are immunoreactive or immunospecific for and therefore specifically and selectively bind to a $PrP^{Sc}$ protein or a soluble protein of the invention. Antibodies which are immunoreactive and immunospecific for native $PrP^{Sc}$ and a protein of the invention are preferred. Antibodies for $PrP^{Sc}$ and soluble proteins of the invention are preferably immunospecific—i.e., not substantially cross-reactive with related materials. Although the term "antibody" encompasses all types of antibodies (e.g., monoclonal) the antibodies are preferably produced using the phage display methodology described herein.

By "purified antibody" is meant one which is sufficiently free of other proteins, carbohydrates, and lipids with which it is naturally associated. Such an antibody "preferentially binds" to a native $PrP^{Sc}$ protein and a soluble protein of this invention (or an antigenic fragment thereof), i.e., does not substantially recognize and bind to other antigenically-unrelated molecules. A purified antibody of the invention is preferably immunoreactive with and immunospecific for both a protein of the invention and a $PrP^{Sc}$ protein of specific species and more preferably immunospecific for native human $PrP^{Sc}$ a related soluble protein of the invention.

By "antigenic fragment" of a PrP protein is meant a portion of such a protein which is capable of binding an antibody of the invention.

By "binds specifically" is meant high avidity and/or high affinity binding of an antibody to a specific polypeptide i.e., epitope of a $PrP^{Sc}$ protein. Antibody binding to its epitope on this specific polypeptide is preferably stronger than binding of the same antibody to any other epitope, particularly those which may be present in molecules in association with, or in the same sample, as the specific polypeptide of interest e.g., binds more strongly to $PrP^{Sc}$ than denatured fragments of $PrP^{C}$ so that by adjusting binding conditions the antibody binds almost exclusively to $PrP^{Sc}$ and not denatured fragments of $PrP^{C}$. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g. by use of appropriate controls. In general, antibodies of the invention which bind to native $PrP^{Sc}$ in situ with a binding affinity of $10^7$ mole/l or more, preferably $10^8$ mole/liters or more are said to bind specifically to $PrP^{Sc}$. In general, an antibody with a binding affinity of $10^6$ mole/liters or less is not useful in that it will not bind an antigen at a detectable level using conventional methodology currently used.

By "detectably labeled antibody", "detectably labeled anti-PrP" or "detectably labeled anti-PrP fragment" is meant an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels may be selected from a variety of such labels known in the art, but normally are radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin) ), methods for labelling antibodies, and methods for using labeled antibodies are well known in the art (see, for example, Harlow and Lane, eds. (*Antibodies: A Laboratory Manual* (1988) Cold Spring Harbor Laboratory Press, Cold Spring Harbor, N.Y.)).

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes:

(a) preventing the disease from occurring in a subject which may be predisposed to the disease but has not yet been diagnosed as having it;

(b) inhibiting the disease, i.e., arresting its development; or (c) relieving the disease, i.e., causing regression of the disease. The invention is directed toward treating patients with infectious prions and is particularly directed toward treating humans infected with $PrP^{Sc}$, resulting in a disease of the central nervous system such as bovine spongiform encephalopathy; Creutzfeldt-Jakob Disease; fatal familial insomnia or Gerstmann-Straussler-Scheinker Disease.

Abbreviations used herein include:
CNS for central nervous system;
BSE for bovine spongiform encephalopathy;
CJD for Creutzfeldt-Jakob Disease;
FFI for fatal familial insomnia;
GSS for Gerstmann-Straussler-Scheinker Disease;
Hu for human;
HuPrP for a human prion protein;
Mo for mouse;
MoPrP for a mouse prion protein;
SHa for a Syrian hamster;
SHaPrP for a Syrian hamster prion protein;
Tg for transgenic;
Tg(SHaPrP) for a transgenic mouse containing the PrP gene of a Syrian hamster;
Tg(HuPrP) for transgenic mice containing the complete human PrP gene;
Tg(ShePrP) for transgenic mice containing the complete sheep PrP gene;
Tg(BovPrP) for transgenic mice containing the complete cow PrP gene;
$PrP^{Sc}$ for the scrapie isoform of the prion protein;
$PrP^{Sc}$ 106 for the scrapie isoform of the prion protein that is soluble in mild detergents consisting of residues 89–140 and 177–230;
$PrP^{C}$ for the cellular contained comon, normal isoform of the prion protein;
$MoPrP^{Sc}$ for the scrapie isoform of the mouse prion protein;
MHu2M for a chimeric mouse/human PrP gene wherein a region of the mouse PrP gene is replaced by a corresponding human sequence which differs from mouse PrP at 9 codons;
Tg(MHu2M) mice are transgenic mice of the invention which include the chimeric MHu2M gene;
$MHu2MPrP^{Sc}$ for the scrapie isoform of the chimeric human/mouse PrP gene;
$PrP^{CJD}$ for the CJD isoform of a PrP gene;
$Prnp^{0/0}$ for ablation of both alleles of an endogenous prion protein gene, e.g., the MoPrP gene;
$Tg(SHaPrP^{+/0})81/Prnp^{0/0}$ for a particular line (81) of transgenic mice expressing SHaPrP, +/0 indicates heterozygous;
$Tg(HuPrP)/Prnp^{0/0}$ for a hybrid mouse obtained by crossing a mouse with a human prion protein gene (HuPrP) with a mouse with both alleles of the endogenous prion protein gene disrupted;
$Tg(MHu2M)/Prnp^{0/0}$ for a hybrid mouse obtained by crossing a mouse with a chimeric prion protein gene (MHu2M) with a mouse with both alleles of the endogenous prion protein gene disrupted.
FVB for a standard inbred strain of mice often used in the production of transgenic mice since eggs of FVB mice are relatively large and tolerate microinjection of exogenous DNA relatively well.

OVERVIEW

Modified proteins are provided which retain abnormal properties associated with disease of the native protein but which are made soluble by the modification. The modification can include all or any of adding or replacing amino acids, deleting amino acids or attaching another molecule to the native protein. A preferred embodiment of the invention is an amino acid sequence which is shorter than the native sequence and is obtained by deleting codon segments from DNA expressing a native protein in order to obtain a shorter, soluble protein which mimics characteristics of an insoluble native protein—retains abnormal properties associated with disease. Soluble proteins of the invention are characterized by: (1) including a structural modification from the full length native protein; (2) having a higher degree of solubility than the native protein; (3) retaining the basic abnormal biological characteristics of the native protein such as (a) not being subject to enzymatic digestion and (b) causing disease.

Soluble proteins of the invention can be obtained by providing a DNA sequence which encodes a native protein and systematically removing codons. Copies of the shortened versions of DNA are made and expressed to provide the shortened proteins. The shortened proteins are then tested for solubility. Soluble proteins are then further tested to confirm that they retain the biological characteristics of the native protein.

Other modified soluble proteins of the invention can be prepared and tested in a similar manner. For example, a native sequence can be modified so that particular codons are replaced with new codons which express a different amino acid such as a polar amino acid (e.g., glutamic acid, asparagine glutamine and aspartic acid) which has hydrophilic properties. A large number of sequences can be generated wherein different codons are replaced with new codons such as codons expressing a polar amino acid such as aspartic acid. The modified DNA sequences obtained are then expressed to obtain modified proteins. The modified proteins are tested for solubility. Proteins found to be soluble are further tested to confirm that they retain abnormal properties associated with disease.

Soluble proteins which are larger than a native protein can also be produced in a similar manner. The DNA sequence can be systematically modified by adding codons within the sequence to either end of the sequence. The modified DNA sequence is expressed to provide proteins which are longer than the native protein. The longer proteins are tested for solubility. Proteins found to be soluble are then further tested to confirm that they maintain abnormal properties associated with disease.

In addition to shortening, lengthening or modifying the amino acid sequence by replacing one amino acid with another it is possible to modify the native protein by attaching a new molecular entity. The added molecular entity may be added by attaching it to either terminus of the native protein or attaching it anywhere along the chain. Typical sites of attachment would include replacing an amino acid with an amino acid substitute which includes an "R" group which is entirely different from any naturally occurring amino acid "R" group and which improves the solubility of the protein. For example, the added "R" group can be a highly hydrophilic group. Lastly, it is possible to modify the native proteins by using combinations of all or any of the above-described modifications.

SEQUENCE DETERMINATION

Determining a nucleotide sequence which encodes a native insoluble protein is not part of the present invention. Such sequences are known, for example, the sequences of PrP genes for several different mammals are disclosed within U.S. Pat. No. 5,565,186 issued Oct. 15, 1996 and the sequence or several beta-amyloid proteins related to Alzheimer's disease are disclosed within U.S. Pat. No. 5,387,746 issued Feb. 7, 1995. In addition to nucleotide sequence information, the literature includes significant amounts of information on structural aspects of the protein expressed by the sequences.

After obtaining a sequence of interest, copies are made using conventional methodology, after making the copies, the copies are segregated into groups or pools. For example, the copies can be divided into five or more, ten or more, a hundred or more, etc. groups or pools of sequences. This separation is carried out so that each group or pool can be individually manipulated. Preferably ten or more identical sequences are in each pool.

Once the pools of identical sequences are obtained the sequences within each of the individual pools can be systematically altered. For example, the sequences within each pool can be altered by (1) removing one or more codons (codons can be removed from either end of the protein or from intermediate positions; (2) adding additional codons (codons can be added to either end or added within the native sequence); (3) adding and deleting codons. Depending upon the information known about the protein expressed by the genetic material, it is possible to remove systematically or add DNA segments which will remove or add particular structural features of the express protein. In this way it is possible to delete or add segments so as to provide shortened or lengthened DNA segments, which, when expressed, will create different pools of proteins, i.e., pools of proteins wherein proteins of different pools differ from each other by lacking or having a different significant structural feature.

After expressing the different pools of nucleotides to obtain different pools of proteins, the different pools of proteins are individually tested, first for solubility and thereafter for biological activity. Those proteins which exhibit a significantly higher degree of solubility as compared with the native protein are candidates for further testing. Determining whether the modified protein is soluble can vary depending on the protein being tested. For example, the protein could be tested in pure water, a normal solution similar to human body fluids or in an aqueous solution with a mild detergent. The solvent should be an aqueous solvent and should be chosen such that the native protein is substantially insoluble in the chosen solvent thereby making it possible to characterize the modified protein by its solubility within that solvent. In some instances it is desirable to further insure that the protein is soluble by subjecting the purported solution to a centrifuge at 100,000 g for approximately one hour. If the protein is not precipitated out and remains in the supernatant the protein is judged to be soluble. Those skilled in the art will readily identify other solubility tests which are suitable for use with particular proteins.

Soluble proteins which are identified are then tested by another assay such as the ability of the protein to be digested with a specific enzyme, which does not digest the insoluble native protein. If the protein is not digested, it is then subjected to further biological testing such as formulating the protein and inoculating an animal with the protein. The inoculated animal is observed to determine if the animal develops disease as a result of the inoculation. Transgenic animals which exhibit disease after inoculation with an infectious prion are disclosed with U.S. Pat. No. 5,565,186 issued Oct. 15, 1996, incorporated herein by reference to disclose and describe such transgenic animals and methods of testing compounds using such transgenic animals.

INSOLUBLE PROTEINS

Soluble proteins of the present invention are modifications of insoluble native proteins which are associated with specific diseases. The invention is applicable to the modification of proteins which are yet to be discovered. However, the invention can now be applied directly to known insoluble native proteins which are associated with particular diseases. The following is a non-limiting list of diseases with associated insoluble proteins.

| Disease | Insoluble Proteins |
| --- | --- |
| Alzheimer's Disease | APP, Aβ peptide, α1-antichymotrypsin, tan, non-Aβ component |
| Prion diseases, Creutzfeld Jakob disease, scrapie and bovine spongeform encephalopathy | PrP$^{Sc}$ |
| ALS | SOD and neurofilament |
| Pick's disease | Pickbody |
| Parkinson's disease | Lewy body |
| Diabetes Type 11 | Amylin |
| Multiple myeloma-plasma cell dyscrasias | IgL-chain |
| Familial amyloidotic polyneuropathy | Transthyretin |
| Medullary carcinoma of thyroid | Procalcitonin |
| Chronic renal failure | β$_2$-microglobulin |
| Congestive heart failure | Atrial natriuretic factor |
| Senile cardiac and systemic amyloidosis | Transthyretin |
| Chronic inflammation | Serum amyloid A |
| Atherosclerosis | ApoA1 |
| Familial amyloidosis | Gelsolin |

It should be noted that the insoluble proteins listed above each include a number of variance or mutations which are intended to be encompassed by the present. Known pathogenic mutations and polymorphisms in the PrP gene related to prion diseases are given below and the sequences of human, sheep and bovine are given in U.S. Pat. No. 5,565, 1865, issued Oct. 15, 1996.

MUTATION TABLE

| Pathogenic human mutations | Human Polymorphisms | Sheep Polymorphisms | Bovine Polymorphisms |
|---|---|---|---|
| 2 octarepeat insert | Codon 129 Met/Val | Codon 171 Arg/Glu | 5 or 6 octarepeats |
| 4 octarepeat insert | Codon 219 Glu/Lys | Codon 136 Ala/Val | |
| 5 octarepeat insert | | | |
| 6 octarepeat insert | | | |
| 7 octarepeat insert | | | |
| 8 octarepeat insert | | | |
| 9 octarepeat insert | | | |
| Codon 102 Pro-Leu | | | |
| Codon 105 Pro-Leu | | | |
| Codon 117 Ala-Val | | | |
| Codon 145 Stop | | | |
| Codon 178 Asp-Asn | | | |
| Codon 180 Val-Ile | | | |
| Codon 198 Phe-Ser | | | |
| Codon 200 Glu-Lys | | | |
| Codon 210 Val-Ile | | | |
| Codon 217 Asn-Arg | | | |
| Codon 232 Met-Ala | | | |

It should also be noted that such proteins often have two different 3-dimensional conformations with the same amino acid sequence. One conformation is associated with disease characteristics and is generally insoluble whereas the other conformation is not associated with disease characteristics and is soluble. The present invention endeavors to modify the insoluble proteins in a manner which makes them soluble but which allows them to retain substantially all of their characteristics associated with the disease. Thus when a soluble protein of the invention is used to inoculate an animal the animal will develop the disease.

SYNTHESIZING SOLUBLE PROTEINS

Soluble proteins of the invention have at least two characteristics in common. First, they are substantially more soluble than the insoluble native protein from which they are derived or which they are based on. Second, they continue to possess the abnormal properties of the native protein associated with disease. The soluble proteins of the invention can be divided into a number of different categories. First, the soluble proteins may have a lesser number of amino acids than the native insoluble proteins. Other soluble proteins of the invention have a greater number of amino acids than the insoluble native protein. Still others may have the same number of amino acids but have different amino acids with some deleted or added relative to the native insoluble protein. In another embodiment the native protein is chemically modified by including alternate amino acids or by attaching chemical side chains which improve the solubility of the molecule. Lastly, soluble proteins of the invention can include variations of all of the above. Soluble proteins of the invention which include lesser, greater or different amino acids as compared to the insoluble native form can be produced chemically or by the use of molecular genetics. Because it is often desirable to produce large number of different proteins initially, for testing, it is generally preferable to produce such proteins by the use of molecular genetics. Proteins which include lesser or greater numbers of amino acids or simply different amino acids as compared to the native protein can be produced by the use of molecular genetics in a manner described below.

Although it is not necessary to know the sequence it is necessary to have isolated the sequence which, when expressed, produces the insoluble native protein. Once this genetic material is isolated it can be systematically modified. For example, a DNA sequence containing 100 codons could be copied and divided into 100 different pools. In each pool a different codon is removed. A variety of alternative systematic deletions will be apparent to those skilled in the art. For example, every fifth codon could be deleted or groups of codons could be deleted at specific terminal or internal areas of the sequence.

In the same manner it is possible to ligate the DNA sequence at any desired point and add one or more additional codons. When codons are added it is preferred to add codons which encode polar amino acids and particularly preferred to add codons which encode acidic polar amino acids in that these amino acids tend to provide increase solubility to the resulting protein. Those skilled in the art will recognize that it is also possible to simultaneously delete some codons and add other codons so as to arrive at the same number of original codons as encode the native insoluble protein or to arrive at a modified sequence which includes a lesser or greater number of codons as compared to the sequence encoding the native protein.

Using methodology such as that disclosed in U.S. Pat. No. 5,182,366 to Huebner, et al it is possible to generate thousands, tens of thousands and even millions of different variations of a desired sequence in a relatively short period of time.

When desired sequences have been generated the sequences are then placed in a suitable expression vector using technology well known to those skilled in the art. The expression vector is then placed in a suitable host and expressed to obtain a large number of different amino acid sequences. The amino acid sequences are then assayed using the concepts of the present invention in order to determine which sequences are soluble. The soluble sequences are then further tested in order to determine if they continue to retain the abnormal properties associated with disease which properties are possessed by the native insoluble protein. Those proteins which are both soluble and possess the abnormal properties associated with disease are proteins of the invention.

Chemical synthesis methodology can be used to produce additional variants which variants can also be tested for solubility and for biological activity with respect to maintaining the abnormal properties associated with disease which are possessed by the native insoluble protein. The chemical synthesis methodologies can be applied to produce proteins which include non-coded amino acids. Further, the amino acid sequence can be chemically synthesized to include optical isomers of the naturally occurring amino acids i.e., the D-forms. Various non-coded amino acids and methods of producing millions of variations of such are disclosed within U.S. Pat. No. 5,420,246, issued to Rutter, et al on May 30, 1995. Chemical methodologies make it possible to produce a large number of different variations of amino acids. An example of such is disclosed within PCT Publication WO94/06451 to Zuckerman, et al published Mar. 31, 1994. When carrying out such methodologies for purposes of the present invention the "R" groups of the amino acids or amino acid substitutes are generally polar groups which provide a hydrophilic property to the molecule as a whole thereby improving the solubility characteristics of the molecule.

Although chemical synthesis methodologies can be used to produce soluble molecules those soluble molecules may be less useful in terms of the generation of antibodies. Antibodies generated using such molecules may have an affinity for sites which do not exist on the native insoluble molecule. Thus, for purposes of the present invention, it is preferred to use the "shorter" amino acid sequences which are soluble in order to generate antibodies which bind not only to the soluble shorter sequence but to the full length native insoluble sequence.

PRODUCING ANTIBODIES

When soluble proteins of the invention have been created and tested for biological activity, those proteins are extremely useful in generating antibodies which bind to the native protein as well as the soluble protein. Such antibodies can be produced by first inoculating a host animal with a native insoluble protein (or alternatively, a soluble protein in the invention). The host animal may be any animal, and is preferably a host animal of the type defined herein such as a mouse, rat, guinea pig, or hamster and is most preferably a mouse. The host animal is inoculated with proteins which are endogenous to a different species which is preferably a genetically diverse species as defined herein. For example, a transgenic mouse is inoculated with human $PrP^{Sc}$. The inoculated host animal will then generate antibodies. It is preferable to inoculate an animal which has the endogenous gene which expresses the protein ablated. For example, a mouse which has its endogenous PrP gene ablated which mouse is described in U.S. Pat. No. 5,565,186. A generalized method of ablating an endogenous gene is described in U.S. Pat. No. 5,464,764, issued Nov. 7, 1995 to Capecchi, et al.

After allowing for the generation of antibodies the mouse is sacrificed and bone marrow and spleen cells are removed. The cells are lysed, RNA is extracted and reversed transcribed to cDNA. Antibody heavy and light chains (or parts thereof) are then amplified by PCR. The amplified cDNA library may be used as is or after manipulation to create a range of variants and thereby increase the size of the library.

An IgG phage display library is then constructed by inserting the amplified cDNA encoding IgG heavy chain and the amplified cDNA encoding a light chain into a phage display vector (e.g., a pComb3 vector) such that one vector contains a cDNA insert encoding a heavy chain fragment in a first expression cassette of the vector, and a cDNA insert encoding a light chain fragment in a second expression cassette of the vector.

Ligated vectors are then packaged by filamentous phage M13 using methods well known in the art. The packaged library is then used to infect a culture of E. coli, so as to amplify the number of phage particles. After bacterial cell lysis, the phage particles are isolated and used in a panning procedure.

The soluble proteins of the present invention are invaluable in the panning procedure. Because the proteins are soluble, they can be more readily brought into contact with the phage particles to determine which phage are expressing antibodies which bind proteins of the invention. The proteins of the invention can be labeled in order to more readily detect when binding occurs. Those phage which bind proteins of the invention are then isolated and cloned. The genetic material can be placed into cells to produce antibodies. The cells can be fused with suitable melanoma cells in order to create hybridomas for the production of monoclonal antibodies.

EXAMPLES

The following examples are put forth so as to provide those of ordinary skill in the art with a complete disclosure and description of how to make soluble proteins and carry out the methodology for finding such proteins, and are not intended to limit the scope of what is regarded as the invention. Efforts have been made to insure accuracy with respect to numbers used (e.g., amounts, temperature, etc.) but some experimental errors and deviations should be accounted for. Unless indicated otherwise, parts or parts by weight, molecular weight is weight average molecular weight; temperature is in degrees centigrade; and pressure is at or near atmospheric.

Example 1

Removing Segments of PrP

In a specific embodiment segments of the PrP molecule were systematically removed. Specifically regions of putative secondary structure in $PrP^C$, Z. Huang, et al., *Proc. Natl. Acad. Sci. USA* 91, 7139–7143 (1994) were systematically removed. Deletion of each of the four putative helices prevented $PrP^{Sc}$ formation. However, removal of a 36 residue loop between helices two and three was not deleterious. A resulting $PrP^{Sc}$ molecule was designated $PrP^{Sc}$ 106 in that it contains 106 amino acids after cleavage of an N-terminal signal peptide and a C-terminal sequence for addition of a glycolipid anchor. While $PrP^{Sc}$ 106 exhibited resistance to digestion by proteinase K, it was soluble in 0.5% Sarkosyl. The discovery of $PrP^{Sc}$ 106 greatly facilitates structural studies of $PrP^{Sc}$, as well as investigations of the mechanism of $PrP^{Sc}$ formation and the production of $PrP^{Sc}$ specific antibodies.

During the conversion of $PrP^C$ into $PrP^{Sc}$, PrP undergoes a profound conformational change, K. M. Pan, et al., *Proc. Natl. Acad. Sci. USA* 90, 10962–10966 (1993). This structural transition is accompanied by the acquisition of insolubility in non-denaturing detergents and resistance to digestion by proteinase K, S. B. Prusiner, et al., *Biochemistry* 21, 6942–6950 (1982); R. K. Meyer, et al., *Proc. Natl. Acad. Sci. USA* 83, 2310–2314 (1986). Structural studies of $PrP^{Sc}$ have been limited by the insolubility of the molecule. S. B. Prusiner, et al., *Cell* 35, 349–358 (1983); B. W. Caughey, et al., *Biochemistry* 30, 7672–7680 (1991); M. Gasset, et al., *Proc. Natl. Acad. Sci. USA* 90, 1–5 (1993); J. Safar, et al., *J. Biol. Chem.* 268, 20276–20284 (1993). However, synthetic and recombinant fragments of PrP analogous to $PrP^C$ have been more amenable to structural investigations, H. Zhang, et al., *J. Mol. Biol.* 250, 514–526 (1995); I. Mehlhorn, et al., *Biochemistry* 35, 5528–5537 (1996); R. Riek, et al., *Nature* 382, 180–182 (1996). Studies are limited not only by insolubility but by difficulties in achieving high level expression of undegraded recombinant PrP. I. Mehlhorn, et al.,

17

*Biochemistry* 35, 5528–5537 (1996); M. Scott, et al., *Protein Engineering* 2, 69–76 (1988).

Example 2

Cloning PrP

Molecular cloning of a cDNA encoding chicken PrP was carried out to study the structural features of mammalian PrP by molecular modeling. Four regions of putative secondary structure were identified using several structure prediction algorithms, Z. Huang, et al., *Proc. Natl. Acad. Sci. USA* 91, 7139–7143 (1994); M. Gasset, et al., *Proc. Natl. Acad. Sci. USA* 89 10940–10944 (1992). Although there was disagreement as to whether certain regions adopt α-helical or β-sheet structures, all the analyses predicted these regions would adopt secondary structure. Accordingly, synthetic peptides were produced corresponding to each of the four regions designated Hi, H2, H3 and H4. In aqueous buffers H1, H3 and H4 unexpectedly adopted β-sheet structures, M. Gasset, et al., *Proc. Natl. Acad. Sci. USA* 89 10940–10944 (1992).

Example 3

Structural Analysis

Mixing H1 in a β-sheet conformation with H2 in a coil acted to convert H2 into β-sheet, J. Nguyen, et al., *Biochemistry* 34, 4186–4192 (1995). A longer peptide of 56 residues containing H1 and H2 adopted an α-helical conformation in aqueous buffers exhibited chemical shifts indicating an α-helix in the H1 region, H. Zhang, et al., *J. Mol. Biol.* 250, 514–526 (1995). The secondary structure as determined by NMR in the H2 region was less clear. The H3 and H4 regions were identified in NMR studies of a C-terminal fragment of 111 residues, R. Riek, et al., *Nature* 382, 180–182 (1996). Those studies also identified a short α-helix in the loop between H2 and H3 as well as short β-sheet consisting of residues 128–131 and 161–164 forming antiparallel strands.

Figure 1:
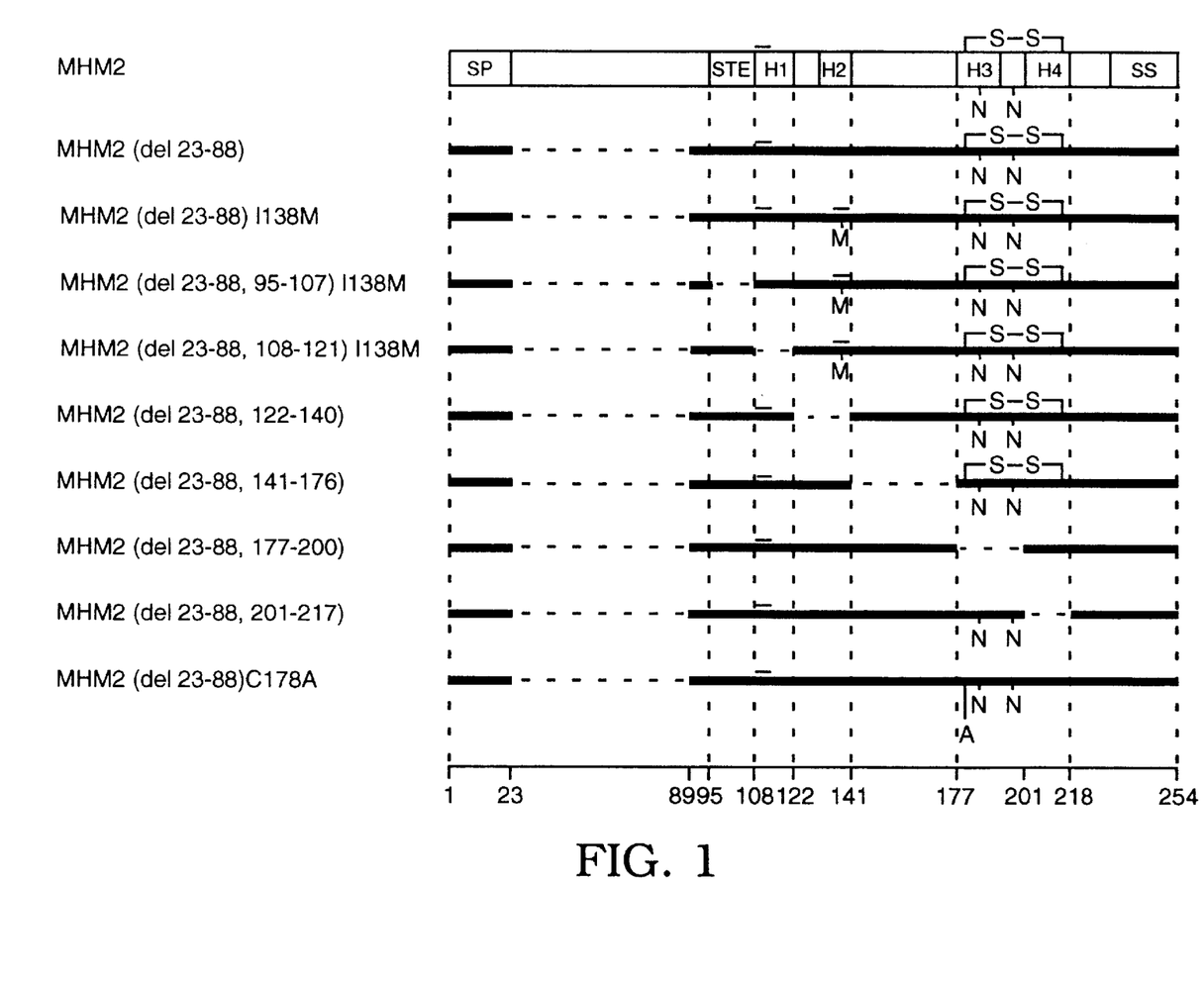
FIG. 1 is a map of regions of secondary structure of protein expressed by a PrP gene in terms of the requirement for each region of the protein to support the formation of $PrP^{Sc}$.

Based on the molecular model PrP$^C$ as well as data from CD and FTIR studies, systematic tests of the model in terms of the ability of mutagenized prP$^C$ molecules to be converted into PrP$^{Sc}$ were carried out. The studies were done in both cultured neuroblastoma (N2a) cells and transgenic (Tg) mice. As a result there is provided a map of the regions of putative secondary structure in terms of the requirement for each region to support the formation of PrP$^{Sc}$ (FIG. 1).

Example 4

Epitope Tags—Antibodies

Studies were performed in scrapie infected N2a cells (ScN2a) using a epitope-tagged molecule MHM2 PrP$^C$ which had been shown previously to be converted into MHM2 PrP$^{Sc}$ in ScN2 cells, A. Taraboulos, et al., *Proc. Natl. Acad. Sci. USA* 87, 8262–8266 (1990); M. Rogers, et al., *Immunol.* 147, 3568–3574 (1991); M. R. Scott, et al., *Protein Sci.* 1, 986–997 (1992). All the PrP constructs to be expressed in ScN2a cells were cloned into the pSPOX.llneo vector and the cells transiently transfected, M. R. Scott, et al., *Protein Sci.* 1, 986–997 (1992).

The epitope-tagged MHM2 PrP has two Met residues at positions 108 and 111 that are found in SHa and Hu PrP. This epitope is recognized by the α-PrP 3F4 mAb, M. Rogers, et al., *Immunol.* 147, 3568–3574 (1991); R. J. Kascsak, et al., *J. Virol* 61, 3688–3693 (1987). Since PrP$^C$ encoded by MHM2 was readily converted into PrP$^{Sc}$ in ScN2a cells, it

18 could be used to assess the effect of selective deletions of specific domains within the PrP molecule (FIG. 1).

Example 5

Expression in ScN2a Cells

MHM2 in which the N-terminal region consisting of residues 23–88 had been deleted was used as a starting material. This construction supported PrP$^{Sc}$ formation in ScN2a cells as evidenced by the production of a α-PrP 3F4 mAb reactive protein that was resistant to digestion by proteinase, M. Rogers, et al ., *Proc. Natl. Acad. Sci. USA* 90, 3182–3186 (1993). When residues 33–80 of MoPrP were deleted the resulting construct was shown to render PrnP$^{O/O}$ mice susceptible to Mo scrapie prions, M. Fischer, et al., *EMBO J.* 15.

Three regions of putative secondary structure designated H2, H3 or H4 were deleted. In separate constructs the H2, H3 and H4 regions were deleted from the N-terminally truncated MHM2 PrP construct in which residues 23–88 had been deleted. Each of these deleted PrPs was then expressed in ScN2a cells. The H2 (residues 122–140), H3 (residues 177–200) and H4 (residues 201–217) regions were deleted and each construct expressed in ScN2a cells was detected by α-PrP 3F4 mAb immunostaining. The H3 deletion which no longer contains both consensus sites for Asn-linked glycosylation, C. Locht, et al., *Proc. Natl. Acad. Sci. USA* 83, 6372–6276 (1986) migrated as a band of $M_r$ ~kDa. Two other constructs were also expressed: one with a deletion of the loop between H2 and H3 containing 36 Residues (141–176) and the other with a point mutation at residue 178 where Ala was substituted for Cys to prevent the formation of a disulfide bond between this residue and Cys 213.

Example 6

Proteinase K Resistance

Deletion of the H2, H3 and H4 regions as well as mutagenesis of Cys 178 prevented PrP$^{Sc}$ formation as judged by resistance to digestion with proteinase K (20 ug/ml, 30 min, 37° C.). The results showed that MHM2 was converted into a protease resistant isoform as was the N-terminally deleted molecule missing residues 23–88.

Deletion of the loop between H2 and H3 containing 36 residues (141–176) did not prevent conversion of the molecule into a protease resistant isoform. The acquisition of protease-resistance during PrP$^{Sc}$ formation seems to occur within caveolae-like domains (CLDs) and PrP$^C$ is targeted to CLDs by its GPI anchor. A. Taraboulos, et al., *J. Cell Biol.* 129, 121–132 (1995). Cells expressing the construct with the loop deletion were exposed to PIPLC. The results showed that virtually all of the protease digestible MHM2 (del 23–88, 141–176), designated PrP 106 was released by the enzyme. N. Stahl, et al., *Cell* 51, 229–240 (1987). This indicates that PrP 106 transits from the ER to the cell surface where it is bound by a GPI anchor as is full length PrP$^C$.

Example 7

(STE) Region Removed

An analysis of the deletion of H1 containing residues 108–121 was carried out by creating an 1138M mutation in order to produce a SHaPrP epitope detectable by the α-PrP 13A5 mAb M. Rogers, et al., *J. Immunol.* 147, 3568–3574 (1991; R. A. Barry, et al, *J. Infect. Dis.* 154, 518–521 (1986). Like the deletion of H2–H4, removal of H1 prevented PrP$^{Sc}$ formation. Thereafter, α-PrP 13A5 mAbs were used to study deletion of the stop transfer effector (STE) region composed of residues 95–107 adjacent to H1 which has been implicated in controlling the translocation of PrP synthesized in cell free systems with dog pancreas microsomal membranes. C. S. Yost, et al., *Nature* 343, 669–672 (1990). Like the deletions of H1–H4, removal of the STE region also prevented PrP$^{Sc}$ formation.

Based on the foregoing results, the shift in M$_r$ values were examined after limited digestion with proteinase K for PrP$^{Sc}$ 106. In the absence of proteinase K, both the MHM2 PrP$^C$ and PrP$^{Sc}$ isoforms encoded by the transfected constructs were immunostained with αPrP 3F4 mAbs. The broad range of $M_r$ values is presumably due to aberrant Asn-linked glycosylation. After limited proteolysis the $M_r$ values were decreased and the range of molecular $M_r$ values diminished. Based on the shift in $M_r$ values, it seems likely that a few amino acid residues may have been removed from the N-terminus of $PrP^{Sc}$ 106 during limited proteolysis. Microsequencing can provide resolution of this issue.

Example 8

Solubility

Insolubility in non-denaturing detergents has been an invariant feature of protease-resistant $PrP^{Sc}$. R. K. Meyer, et al., *Proc. Natl. Acad. Sci. USA* 83, 2310–2314 (1986); S. B. Prusiner, et al., *Cell* 35, 349–358 (1983). Knowing such, ScN2a cells expressing PrP 106 were lysed in increasing concentrations of N-lauroylsarcosine (Sarkosyl). The suspensions were centrifuged at 100,000×g for 1 h at 20° C. At a concentration of 0.5% Sarkosyl or greater, all of the $PrP^{Sc}$ 106 was found in the supernatant. When the blot was reprobed to detect $MoPrP^{Sc}$ with α-PrP rabbit polyclonal R073 antiserum, all the immunostaining was found in the pellet fraction and none in the supernatant.

Example 9

Structural Analysis

Results obtained show that all of four putative helical regions identified by molecular modeling and the STE region discovered in cell-free translation studies are required for $PrP^{Sc}$ formation. The results also show that the disulfide bond between Cys residues 178 and 213 found in both $PrP^C$ and $PrP^{Sc}$, E. Turk, et al., *J. Biochem.* 176, 21–30 (1988) is essential for $PrP^{Sc}$ formation. Although disruption of this disulfide by the C178A mutation diminished conversion of this mutated $PrP^C$ into $PrP^{Sc}$ treatment of fractions highly enriched for scrapie infectivity with either 2% β-mercatoethanol or 100 mM Dithiothreitol did not diminish prion titers as measured by bioassays in Syrian hamsters. S. B. Prusiner, et al., *Biochemistry* 19, 4883–4891 (1980).

When recombinant PrP (90–231) corresponding to the residues found in PrP 27–30 (the protease resistant core of $PrP^{Sc}$) was refolded after purification under denaturing conditions, it adopted a structure with high α-helical content similar to mammalian $PrP^C$ upon formation of the disulfide bond. I. Mehlhorn, et al., *Biochemistry* 35, 5528–5537 (1996). The disulfide is believed to stabilize the C-terminal α-helices i.e., H3 and H4. Z. Huang, et al., *Proc. Natl. Acad. Sci. USA* 91, 7139–7143 (1994); Z. Huang, et al., *Folding & Design* 1, 13–19 (1996). This is supported by NMR structural studies of a C-terminal fragment of recombinant PrP (121–231) expressed in *E. coli.* R. Riek, et al., *Nature* 382, 180–182 (1996). It is unknown whether rPrP(121–231) which lacks the N-terminal 99 amino acids as well as the Asn-linked CHOs and the GPI anchor reflects accurately the structure of the C-terminal region of $PrP^C$. However, data from the study of rPrP(121–231) demonstrated α-helices that were predicted for the H3 and H4 regions.

Example 10

Characteristics of Prp 106

PrP 106, which lacks residues 23–88 and 141–176 is converted into a $PrP^{Sc}$ like molecule. This supports the position that the short region of β-sheet formed by two antiparallel β-strands consisting of residues 128–131 and 161–164 is unlikely to be the nidus at which $PrP^{Sc}$ is initiated. R. Riek, et al., *Nature* 382, 180–182 (1996). Furthermore, the third α-helix (144–154) found in rPrP (121–231) within the putative loop of $PrP^C$, which was predicted to have an unstable conformation, is also not required for the acquisition of resistance to limited proteolysis.

The results shown here are the first to uncouple the protease-resistance and insolubility of $PrP^{Sc}$. Such results support the position that aggregation which must contribute to the insolubility of purified $PrP^{Sc}$ is not required for protease resistance.

Recent cell-free mixing studies of the binding of partially denatured $PrP^C$ to $PrP^{Sc}$ have argued that the protease-resistance exhibited by radiolabelled $PrP^C$ is inseparable from its binding to the $PrP^{Sc}$ aggregates. D. A. Kocisko, et al., *Nature* 370, 471–474 (1994); B. Caughey, et al., *Jr. Chem. Biol.* 2, 807–817 (1995). However, the present results demonstrate that insolubility and protease-resistance are separable. These results do coincide with earlier studies in which PrP 27–30 in rod shaped aggregates was dispersed into liposomes and remained resistant to proteolytic digestion. R. Gabizon, et al., *J. Biol. Chem.* 263, 4950–4955 (1988).

The $PrP^{Sc}$ 106 shown is less soluble than full length $PrP^C$ but substantially more soluble than full length $PrP^{Sc}$. This suggests that the interaction between $PrP^{Sc}$ 106 molecules (or protease-resistant units composed of $PrP^{Sc}$ 106 molecules) is disrupted by detergents more easily than the interaction between full length $PrP^{Sc}$ molecules.

Using Tg mice with a PrP-ablated background to study the formation of $PrP^{Sc}$ 106 will confirm that $PrP^{Sc}$ 106 supports prion infectivity. Further study to determine whether $PrP^{Sc}$ 106 supports amyloidogenicity in vivo as well as in vitro might demonstrate that an uncoupling of infectivity and amyloidogenicity is linked to the solubility of the molecule.

The unique intermediate solubility of $PrP^{Sc}$ 106 will simplify its purification. First, $PrP^{Sc}$ 106 will be separated from PrP 106 using weak detergents, then separated from other $PrP^{Sc}$ molecules using stronger detergents. Omitting the protease-digestion procedure from purification protocols will be advantageous for structural studies which might be disrupted by the presence of proteases.

Example 11

Antibody Formation

The ability of ScN2a cells to form a protease-resistant but soluble $PrP^{Sc}$ molecule will simplify the isolation of $PrP^{Sc}$-specific antibodies by phage display. Specifically, finding a $PrP^{Sc}$ antibody will be greatly facilitated by panning and screening against a soluble compound such as a soluble $PrP^{Sc}$ 106 molecule. R. A. Williamson, et al., *Proc. Natl.*

Acad. Sci. USA 93 7279–7282 (1996). Determining the tertiary structure of PrP$^{Sc}$ should be substantially advanced by availability of PrP$^{Sc}$ 106 as should be deciphering of the mechanism by which PrP$^{C}$ is converted into PrP$^{Sc}$. The formation of a soluble form of PrP$^{Sc}$ in ScN2a cells may also facilitate development of an effective pharmacotherapeutic for prion diseases. F. E. Cohen, et al., *Science* 264, 530–531 (1994). Further, soluble proteins of the invention such as PrP 106 and variations thereof can, themselves, be tested for their effect on slowing the progression of disease associated with PrP$^{Sc}$. Since the prion diseases are unprecedented in biology and medicine, it is likely that the design of a drug to treat these disorders will require a detailed understanding of the structural transition that PrP undergoes as PrP$^{Sc}$ is formed. With the possibility that bovine prions have been transmitted to people in Britain and France causing vCJD G. Chazot, et al., *Lancet* 347, 1181 (1996); R. G. Will, et al., *Lancet* 347, 921–925 (1996), the development of an effective therapy for prion diseases has acquired paramount importance.

When using soluble proteins of the invention to generate antibodies it is generally preferable to use soluble proteins which include a smaller number of amino acids than the insoluble native protein. By using smaller proteins it is possible to avoid the generation of antibodies which bind to amino acids which have been added which antibodies might be irrelevant in terms of having binding affinity to the native insoluble protein.

The instant invention is shown and described herein in what is considered to be the most practical, and referred embodiments. It is recognized, however, that departures may be made therefrom, which are within the scope of the invention, and that obvious modifications will occur to one skilled in the art upon reading this disclosure.

What is claimed is:

1. A soluble form of a PrP$^{Sc}$ protein characterized by:

(a) comprising less amino acids than a native PrP$^{Sc}$ protein;

(b) causing a prion disease when an animal is inoculated with the soluble protein; and (c) being at least twice as soluble as the native PrP$^{Sc}$ protein in an aqueous solution.

2. The soluble protein of claim 1, wherein the protein is produced by a process comprising the step of:

removing one or more codons at different positions from a plurality of DNA sequences encoding the native insoluble protein to provide a plurality of DNA sequences which differ from each other by one or more codons removed;

expressing the plurality of DNA sequences to obtain a plurality of proteins;

isolating a protein with a greater solubility and the ability to cause the prion disease.

3. The soluble protein of claim 1, wherein the soluble protein is at least five times as soluble as the native PrP$^{Sc}$ protein in an aqueous solution.

4. The soluble protein as claimed in claim 1, wherein the soluble protein is further characterized by:

(d) remaining in supernatant of an aqueous solution when subjected to 100,000 g for one hour.

* * * * *